United States Patent [19]

Kramer et al.

[11]  4,174,348
[45]  Nov. 13, 1979

[54] PREPARATION OF CYCLOPROPANECARBONITRILES

[75] Inventors: Petrus A. Kramer; Helena Austermühle-Bertola, both of Amsterdam, Netherlands

[73] Assignee: Shell Internationale Research Maatschappij B. V., Netherlands

[21] Appl. No.: 910,882

[22] Filed: May 30, 1978

[51] Int. Cl.$^2$ .................................................. C07C 121/46
[52] U.S. Cl. ........................................ 260/464; 562/506
[58] Field of Search ............................................. 260/464

[56] References Cited

U.S. PATENT DOCUMENTS 4,000,180   12/1976   Punja .................................... 260/464

OTHER PUBLICATIONS

Den Basten et al., Journal of Chemical and Engineering Data, vol. 15, No. 3, pp. 453–454 (1970).
Yves Clenet, Bull. Soc. Chim. Fr. 5, pp. 1715–1716 (1966).

*Primary Examiner*—Dolph H. Torrence
*Attorney, Agent, or Firm*—Pravel, Gambrell, Hewitt, Kirk, Kimball & Dodge

[57] ABSTRACT

A novel process is disclosed for the preparation of cyclopropanecarbonitriles of the general formula:

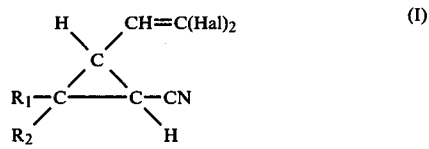

wherein $R_1$, $R_2$ and Hal have the meanings given in the description; which comprises heating the corresponding ammonium or aminium cyclopropanecarboxylate in the presence of a polar aprotic solvent. The process produces cyclopropanecarbonitriles, in high yields, which are useful as intermediates in the production of insecticidally active compounds.

7 Claims, No Drawings

PREPARATION OF CYCLOPROPANECARBONITRILES

BACKGROUND OF THE INVENTION

This invention relates to a process for the preparation of cyano-substituted cyclopropane derivatives, referred to herein generally as cyclopropanecarbonitriles, which can readily be converted by known methods into their corresponding cyclopropane carboxylic acids. Such carboxylic acids, for example, 2-(2,2-dihalovinyl)-3,3-dialkylcyclopropanecarboxylic acids and their corresponding alkyl esters are key intermediates in the manufacture of a group of compounds known as "synthetic pyrethoids" which exhibit remarkable levels of insecticidal and acaricidal activity. United Kingdom Pat. No. 1,413,491 discloses and claims an important group of these synthetic pyrethoids and also demonstrates the difficulties in synthesizing the cyclopropane carboxylic acid precursors thereof.

The compounds produced by the process of this invention are valuable intermediates in the preparation of that class of carboxylic acids which in turn are used to produce insecticidally active compounds such as, for example, the alphacyano 3-phenoxybenzyl ester of 2-(2,2-dichlorovinyl)-3,3-dimethylcyclopropanecarboxylic acid as disclosed in example 20 of the United Kingdom Pat. No. 1,413,491.

SUMMARY OF THE INVENTION

The present invention provides a process for the preparation of a cyclopropanecarbonitrile of the general formula:

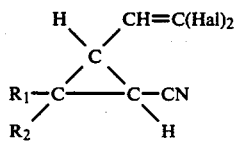

wherein $R_1$ and $R_2$ each individually represent an alkyl group having from one to six carbon atoms and Hal represents a fluorine, chlorine or bromine atom; which comprises heating, in the presence of a polar aprotic solvent, a cyclopropanecarboxylate of the general formula:

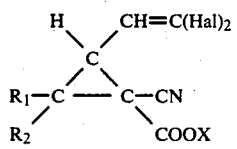

wherein $R_1$, $R_2$ and Hal in the general formula II have the same meaning as in the general formula I, and X in the general formula II representing a quaternary ammonium group. A quaternary ammonium group is defined as the group obtained by the addition of a proton to the nitrogen atom of ammonia or of a primary, secondary or tertiary amine.

DESCRIPTION OF PREFERRED EMBODIMENT

The process according to the present invention yields the compounds of the general formula I with a high order of selectivity, between, for example, 80 and 90%. By the word "selectivity" is meant the yield of a compound of general formula I, calculated on the amount of the compound of the general formula II that has reacted.

The polar aprotic solvent—which must be capable of dissolving the cyclopropanecarboxylate of the general formula II—may, for example, be N,N-dimethylformamide, N,N-dimethylacetamide, dimethyl sulphoxide, N-methylpyrrolidone or acetonitrile. The amount of reaction of the compound of the general formula II after the same time of heating is usually highest with N,N-dimethylformamide.

The cyclopropanecarboxylates of the general formula II, in which X represents a quaternary ammonium group, may be prepared by contacting ammonia or an amine with a carboxylic acid of the general formula

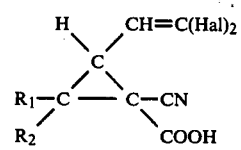

wherein $R_1$, $R_2$ and Hal have the same meaning as in the general formula II. The ammonia or amine may be used in an excess over the stoichiometric amount, the excess may be used in the presence of any other polar aprotic solvent and, although the presence of the aprotic solvent is preferred, the excess of the amine may serve as a solvent for the salt formed therefrom eliminating the need for a different polar aprotic solvent. If desired, the carboxylic acid and the ammonia or amine may be employed in equimolar quantities in the presence of a polar aprotic solvent. Examples of amines which may be used are pyridine, quinoline, isoquinoline, n-hexylamine, aniline, N-methylaniline and N,N-dimethylaniline. The quaternary ammonium group formed by such amines are referred to as pyridinlium, quinolinium, n-hexylaminium, anilinium, N-methylanilinium, and N,N-dimethylanilinium, respectively. Ammonium cyclopropanecarboxylates of the general formula II are preferred.

The temperature and time of heating which are most suitable for a specific starting cyclopropanecarboxylate of the general formula II can easily be found from simple experiments. The temperature will usually be in the range, for example, of from about 100° to about 200° C. The time of heating will usually be between about 10 and about 70 hours, and, of course, depends on the temperature adopted.

$R_1$ and $R_2$ in the general formula II may be the same or different and may represent, for example, a methyl, ethyl, n-propyl, i-propyl, n-butyl, sec-butyl, tert-butyl, n-pentyl or n-hexyl group. $R_1$ and $R_2$ preferably represent methyl groups. Hal preferably represents a chlorine atom. The preferred compound of the general formula II is ammonium 1-cyano-2-(2,2-dichlorovinyl)-3,3-dimethylcyclopropanecarboxylate.

The compounds of general formula II are novel compounds and methods for their preparation are disclosed in a commonly owned co-pending United States patent application, Ser. No. 910,779, entitled "Preparation of Cyano-Substituted Cyclopropane Derivatives" filed concurrently with this application. The disclosure of the above referred to copending application is hereby incorporated by reference as a part of this disclosure.

EXAMPLES I-V

The experiment of Example I was carried out as follows: Ammonia was passed at a temperature of 22° C. through a solution of 6.4 mmol of 1-cyano-2-(2,2-dichlorovinyl)-3,3-dimethylcyclopropanecarboxylic acid in 10 ml of N,N-dimethylformamide until the solution ceased to take up ammonia. The solution thus formed was heated for 18 hours at a temperature of 130° C. Then, the solution was cooled to 22° C. and poured out into 150 ml of water. The mixture thus obtained was extracted with three 15-ml portions of n-pentane. The combined extracts were dried in the presence of anhydrous magnesium sulphate, the magnesium sulphate was removed by filtration and the n-pentane was flashed off. The residue was weighed and its purity determined by the nuclear magnetic resonance (NMR) spectrum.

The raffinate phase, obtained after the extraction with n-pentane and containing unconverted ammonium 1-cyano-2-(2,2-dichlorovinyl)-3,3-dimethylcyclopropanecarboxylate and N,N-dimethylformamide, was acidified with concentrated aqueous hydrochloric acid and the acidic solution was extracted with methylene chloride. The extract phase was dried in the presence of anhydrous magnesium sulphate, the dried solution was boiled down and the residue was weighed. The amount of 1-cyano-2(2,2-dichlorovinyl)-3,3-dimethylcyclopropanecarboxylic acid in the residue was determined by means of NMR analysis. This showed a conversion of the starting ammonium salt of 97%, see column 6 of the table which follows. The selectivity to 2-(2,2-dichlorovinyl)-3,3-dimethylcyclopropanecarbonitrile was 84%, see the table, column 7.

The experiments of Examples II–V were conducted in a manner comparable to the experiment of Example I with the differences stated in columns 2–5 and footnote 4 of the table. In the experiments of examples IV and V 10 ml of N,N-dimethylaniline (79.0 mmol) was used. In the experiment of example IV the above-mentioned ammonium salt was heated. In the experiment of Example V the introduction of ammonia was omitted, so that 6.4 mmol of N,N-dimethylanilinium 1-cyano-2-(2,2-dichlorovinyl)-3,3-dimethylcyclopropanecarboxylate was heated, dissolved in 72.6 mmol of N,N-dimethylaniline. The conversion of the starting compounds and the selectivity to 2-(2,2-dichlorovinyl)-3,3-dimethylcyclopropanecarbonitrile are presented in the table. Those of example V have been estimated by NMR and gas liquid chromatography of the solution at the end of the reaction time.

TABLE

| 1 Example No. | 2 Starting compound[1] | 3 Solvent | 4 Reaction time h | 5 Temp., °C. | 6 Conversion, % | 7 Selectivity % |
|---|---|---|---|---|---|---|
| I | A | N,N-dimethylformamide | 18 | 130 | 97 | 84 |
| II | A | dimethyl sulphoxide | 23 | 125 | 93 | 83 |
| III[4] | A | N-methylpyrrolidone | 17½ | 130 | n.d.[2] | 70[3] |
| IV | A | N,N-dimethylaniline | 64 | 125 | 70 | 86 |
| V | B | " | 64 | 125 | 75 | 80 |

[1] A = ammonium 1-cyano-2-(2,2-dichlorovinyl)-3,3-dimethyl cyclopropanecarboxylate
B = 1-cyano-2-(2,2-dichlorovinyl)-3,3-dimethylcyclopropanecarboxylic acid
[2] not determined
[3] yield of 2-(2,2-dichlorovinyl)-3,3-dimethyl-cyclopropanenitrile, calculated based on starting compound A.
[4] 8.5 mmol of the starting compound used From the foregoing, those of ordinary skill in the art may make modifications and variations of the practice of the invention without departing from the scope of the invention as claimed hereafter.

We claim:

1. A process for the preparation of a cyclopropanecarbonitrile of the general formula:

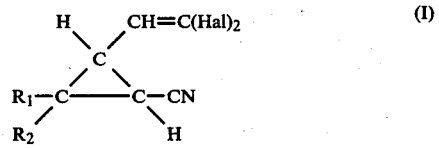

(I)

wherein $R_1$ and $R_1$ each individually represent an alkyl group of from one to six carbon atoms and Hal represents a fluorine, chlorine or bromine atom; which comprises heating, in the presence of a polar aprotic solvent, a cyclopropanecarboxylate of the general formula:

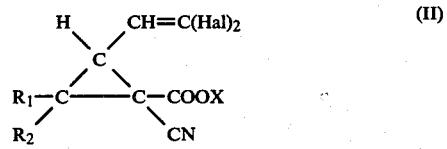

(II)

wherein $R_1$, $R_2$ and Hal in general formula II have the same meanings as in general formula I and X represents a quaternary ammonium group.

2. The process according to claim 1 wherein the polar aprotic solvent is N,N-dimethylacetamide, dimethyl sulphoxide, N-methylpyrrolidone or acetonitrile.

3. The process according to claim 1 wherein the polar aprotic solvent is N,N-dimethylformamide.

4. The process according to claim 1, 2 or 3, wherein the quaternary ammonium group is an ammonium, pyridinium, quinolinium, isoquinolinium, n-hexylaminium, anilinium, N-methylanilinium, or N,N-dimethylanilinium.

5. The process according to claim 1, 2 or 3, wherein heating is effected at a temperature in the range of from about 100° to about 200° C.

6. The process according to claim 4 wherein heating is effected at a temperature in the range of from about 100° C. to about 200° C.

7. A process for the preparation of a cyclopropanecarbonitrile of the general formula:

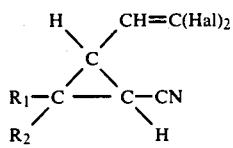

wherein $R_1$ and $R_2$ each individually represents an alkyl group of from one to six carbon atoms and Hal represents a fluorine, chlorine or bromine atom; which comprises (a) contacting a carboxylic acid of the general formula

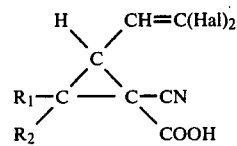

with ammonia or an amine to form a cyclopropanecarboxylate, and (b) heating the cyclopropanecarboxylate in the presence of a polar aprotic solvent.

* * * * *